United States Patent

Krishnamurti et al.

[11] Patent Number: 5,621,153
[45] Date of Patent: Apr. 15, 1997

[54] PROCESS FOR THE PREPARATION OF CHLORO-ALKYLBENZENES AND NOVEL COCATALYSTS THEREFOR

[75] Inventors: Ramesh Krishnamurti, Williamsville; Sandor Nagy, Grand Island; Thomas F. Smolka, West Seneca, all of N.Y.

[73] Assignee: Occidental Chemical Corporation, Niagara Falls, N.Y.

[21] Appl. No.: 426,208

[22] Filed: Apr. 21, 1995

[51] Int. Cl.$^6$ .................... C07C 17/12; C07D 291/02; C07D 327/02
[52] U.S. Cl. .................... 570/209; 549/10; 540/461
[58] Field of Search ................................. 570/209

[56] References Cited

U.S. PATENT DOCUMENTS

| | | | |
|---|---|---|---|
| 1,946,040 | 2/1934 | Stoesser et al. | 260/162 |
| 3,226,447 | 12/1965 | Bing et al. | 260/650 |
| 3,317,617 | 5/1967 | DiBella | 260/650 |
| 4,013,730 | 3/1977 | Graham | 260/650 R |
| 4,031,142 | 6/1977 | Graham | 260/650 R |
| 4,031,144 | 6/1977 | DiBella | 260/650 R |
| 4,031,147 | 6/1977 | Graham | 260/650 R |
| 4,069,263 | 1/1978 | Lin | 260/650 R |
| 4,069,264 | 1/1978 | Lin | 260/650 R |
| 4,250,122 | 2/1981 | Lin et al. | 570/209 |
| 4,289,916 | 9/1981 | Nakayama et al. | 570/209 |
| 4,647,709 | 3/1987 | Wolfram | 570/209 |
| 4,851,596 | 7/1989 | Mais et al. | 570/209 |
| 4,925,994 | 5/1990 | Mais et al. | 570/210 |
| 4,990,707 | 2/1991 | Mais et al. | 570/210 |
| 5,105,036 | 4/1992 | Mais et al. | 570/210 |

FOREIGN PATENT DOCUMENTS

| | | |
|---|---|---|
| 1153746 | 5/1969 | United Kingdom . |
| 1163927 | 9/1969 | United Kingdom . |

Primary Examiner—Mukund J. Shah
Assistant Examiner—King Lit Wong
Attorney, Agent, or Firm—Arthur S. Cookfair; Richard D. Fuerle

[57] ABSTRACT

A process for the para-directed nuclear chlorination of an alkylbenzene, such as toluene, comprises reacting the alkylbenzene with chlorine in the presence of a Lewis acid catalyst and a novel co-catalyst of the formula:

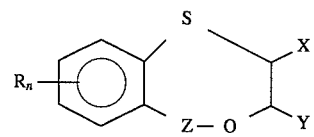

where Z is

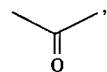

[1]

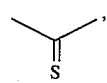

[2]

or

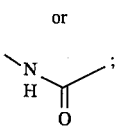

[3]

; and R is Cl, Br, F, $C_1$ to $C_8$ alkyl to $C_1$ to $C_8$ alkoxy; x and y are each hydrogen, or taken together form a fused cyclopentyl or cyclohexyl ring; n is 0, 1 or 2, with the proviso that when Z is [3], n is 0 or 1.

13 Claims, No Drawings

PROCESS FOR THE PREPARATION OF CHLORO-ALKYLBENZENES AND NOVEL COCATALYSTS THEREFOR

BACKGROUND OF THE INVENTION

1. Field of the Invention

This invention relates to a catalyzed process for the para-directed ring chlorination of alkylbenzenes and to novel compounds useful as catalysts. The para-alkylbenzenes, such as para-chlorotoluene, are useful as chemical intermediates for the synthesis of various chemical products, especially agricultural chemical and pharmaceutical products.

2. Prior Art

The production of nuclear chlorinated alkylbenzenes, such as mono-chlorotoluene, is well-known and of considerable commercial importance. Typical commercial processes involve the chlorination of an alkylbenzene, such as toluene, in the presence of a chlorination catalyst, such as ferric chloride, antimony chloride, aluminum chloride, and the like. The usual product of such reactions is a mixture of various monochlorinated and/or polychlorinated compounds. For example, in the liquid phase substitution-chlorination chlorination of toluene by reaction of chlorine and toluene, to form mono-chlorotoluene, the usual product is a mixture of ortho-chlorotoluene and para-chlorotoluene, which may, in addition, contain varying amounts of other chlorinated products such as meta-chlorotoluene, dichlorotoluenes, various polychlorotoluenes and benzylic chlorides.

In the ring chlorination of toluene, since there are two ortho sites and only one para site where substitution may occur, the production of orthochlorotoluene is favored. Because of the greater commercial value of parachlorotoluene, considerable effort has been expended in attempts to direct the chlorination reaction in such a manner as to lower the ratio of orthochlorotoluene to parachlorotoluene, that is, to discover reaction conditions under which the formation of parachlorotoluene is favored.

U.S. Pat. No. 1,946,040 discloses that when alkylbenzenes are reacted with chlorine, the yield of parachlorinated product is improved with the aid of a mixed catalyst comprising sulfur and antimony trichloride and, optionally, iron or lead.

In British Patent No. 1,153,746 (1969) it is disclosed that in the chlorination of toluene in the presence of a ring chlorination catalyst, such as ferric chloride, antimony chloride, and the like, the ratio of orthochloro to parachloro isomers produced may be lowered by the presence of an organic sulfur compound such as thiophene, hexadecylmercaptan, dibenzothiophene or the like.

British Patent No. 1,163,927 (1969) discloses that the formation of parachlorotoluene is enhanced when toluene is reacted with chlorine in the presence of elemental sulfur, or an inorganic sulfur compound, and a ring chlorination catalyst, such as ferric chloride, aluminum chloride, antimony chloride, zinc chloride, iodine, molybdenum chloride, stannous chloride, zirconium chloride, or boron trifluoride.

U.S. Pat. No. 3,226,447 (1965) teaches that in the substitution-chlorination of benzene and toluene, the ratio of ortho isomer to paraisomer in the mono-chlorinated product may be lowered when the reaction is carried out in the presence of an iron, aluminum or antimony halide catalyst and a co-catalyst which is an organic sulfur compound wherein the sulfur is divalent. Examples of such co-catalyst include various mercaptans, mercapto-aliphatic carboxylic acids, aliphatic thiocarboxylic acids, alkyl sulfides, alkyl disulfides, thiophenols, aryl sulfides, aryl disulfides and the like containing divalent sulfur.

According to U.S. Pat. No. 3,317,617 (1967) the formation of parachlorotoluene is favored when toluene is reacted with chlorine in the presence of platinum dioxide.

U.S. Pat. No. 4,031,144 (1977) discloses that a monochlorotoluene product having an unusually high parachlorotoluene content is obtained when toluene is chlorinated in the presence of a catalyst system that contains a ferrocene compound and a co-catalyst that is sulfur or a compound that contains at least one divalent sulfur atom, such as sulfur, sulfur monochloride, sulfur dichloride carbon disulfide, thiophenes, thiophanes, alkylcycloalkyl-, aryl- and aralkyl mercaptans and dimercaptans, thioethers, and the like.

U.S. Pat. No. 4,013,730 (1977) discloses a process for the preparation of monochlorotoluene having a reduced orthochloro- to parachloro isomer content which comprises reacting toluene with chlorine in the presence of a catalyst system comprising a Lewis acid catalyst and, as a co-catalyst, diphenyl selenide or aluminum selenide.

Still further improvements in the preparation of monochlorotoluene having a low ortho to para isomer ratio are disclosed in U.S. Pat. Nos. 4,031,142 and 4,031,147 (1977). U.S. Pat. No. 4,031,142 discloses a process for the preparation of nuclear chlorinated alkylbenzenes, such as monochlorotoluene which comprises reacting an alkylbenzene, such as toluene, with chlorine in the presence of a Lewis acid catalyst and, as a co-catalyst, thianthrene. In accordance with U.S. Pat. No. 4,031,147, even lower ratios of ortho to para isomer are obtained in monochloroalkylbenzene products prepared by the reaction of an alkylbenzene with chlorine in the presence of a Lewis acid catalyst and a thianthrene compound having electron-withdrawing substituents, such as chlorine, present at the 2,3,7 and/or 8 position of the thianthrene nucleus.

U.S. Pat. Nos. 4,069,263 and 4,069,264 disclose processes for the directed nuclear chlorination of alkylbenzenes wherein an alkylbenzene, such as toluene is reacted with chlorine in the presence of a substituted thianthrene having both electron-withdrawing substituents and electron-donating substituents on the nucleus thereof.

U.S. Patent 4,250,122 (1981) to Lin discloses a process for the para-directed chlorination of toluene by reaction with chlorine in the presence of a catalyst mixture prepared by (a) reacting sulfur monochloride with toluene or chlorotoluene in the presence of a Lewis acid catalyst and (b) reacting the reaction product of (a) with chlorine.

U.S. Pat. No. 4,289,916 (1981) to Nakayama et al. teaches a process for producing p-chloroalkylbenzene selectively by chlorinating an alkylbenzene in the presence of a phenoxathiin compound.

U.S. Pat. No. 4,647,709 (1987) to Wolfram discloses a high proportion of p-chlorotoluene is obtained when toluene is chlorinated in the presence of a Lewis acid catalyst and a co-catalyst comprising a chlorination product of 2,8,-dimethylphenoxathiin. The primary component of the co-catalyst is 1,3,7,9-tetrachloro-2,8-dimethylphenoxathiin.

U.S. Pat. No. 4,851,596 (1989) to Mais et al. discloses the ring chlorination of alkylbenzenes in the presence of Friedel-Crafts catalysts and thiazepine compounds as co-catalysts.

U.S. Pat. No. 4,925,994 (1990) to Mais discloses an increase in the proportion of p-chloroalkylbenzenes when alkylbenzenes are chlorinated in the presence of a Friedel-Crafts catalyst and a 1,6-benzothiazocin co-catalyst.

U.S. Pat. No. 4,990,707 (1991) to Mais et al. discloses the nuclear chlorination of alkylbenzenes in the presence of a Friedel-Crafts catalyst and, as a co-catalyst, a benzo-fused imine or benzo[f]-1,4-thiazepine compound to increase the proportional yield of parachloroalkylbenzenes.

U.S. Pat. No. 5,105,036 (1992) to Mais et al. discloses a process for the nuclear chlorination of alkylbenzenes in the presence of Friedel-Crafts catalysts and a co-catalyst which is a cyclic amidine that is oxy-substituted on the exocyclic N atom. The process results in a reaction product containing an increased proportion of the p-chloro isomer.

SUMMARY OF THE INVENTION

In accordance with the present invention, there is provided a process for the production of nuclear chlorinated alkylbenzenes which comprise reacting an alkylbenzene of the formula:

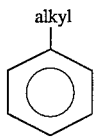

where Alkyl is an alkyl or cycloalkyl radical of up to 12 carbon atoms with a chlorinating agent in the presence of a Lewis acid catalyst and a cocatalyst comprising a compound or mixture of compounds characterized by the formula:

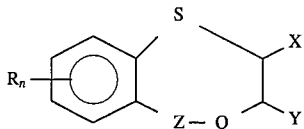

wherein Z is:

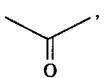 [1]

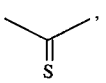 [2]

or

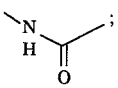 [3]

R is Cl, Br, F, $C_1$ to $C_8$ alkyl, or $C_1$ to $C_8$ alkoxy; x and y are each hydrogen, or taken together form a fused cyclopentyl or cyclohexyl ring; n is 0, 1, or 2, with the proviso that when Z is [3], n is 0 or 1. The preferred cocatalysts are those wherein R is $C_1$–$C_4$ alkyl, most preferably methyl, n is 0 or 1, and X and Y together form a fused cyclopentyl or cyclohexyl ring.

In a second aspect, the present invention comprises a group of novel compounds, useful as catalysts. The novel compounds of this invention are characterized by the formula:

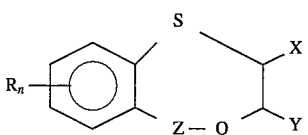

wherein Z is:

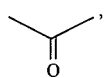 [1]

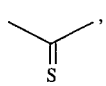 [2]

or

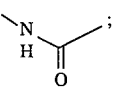 [3]

R is Cl, Br, F, $C_1$ to $C_8$ alkyl, or $C_1$ to $C_8$ alkoxy; X and Y are each hydrogen, or taken together form a fused cyclopentyl or cyclohexyl ring, with the proviso that when Z is [1], X and Y represent a fused cyclopentyl or cyclohexyl ring; n is 0, 1, or 2, with the proviso that when Z is [3], n is 0 or 1.

DETAILED DESCRIPTION OF THE INVENTION

A wide variety of Lewis acid catalysts may be employed in the process of the present invention. The term "Lewis acid catalyst" as employed herein includes, in addition to Lewis acids, those compounds or elements that will form Lewis acids under the conditions of the chlorination reaction. Preferred catalysts for this purpose are compounds of antimony, lead, iron, molybdenum and aluminum, including for example, the halides, oxyhalides, oxides, sulfides, sulfates, carbonyls and elemental form of these elements and mixtures of such compounds and most preferably the chlorides of aluminum, antimony, and iron. Typical of the catalysts which may be employed in the process of this invention are aluminum chloride, antimony trichloride, antimony pentachloride, antimony trioxide, antimony tetraoxide, antimony pentaoxide, antimony trifluoride, antimony oxychloride, molybdenum hexacarbonyl, lead sulfide, ferric chloride, ferrous chloride, ferrous sulfate, ferric oxide, ferrous sulfide, iron disulfide, iron pentacarbonyl, iron metal, and the like.

The preferred co-catalysts which may be employed in the chlorination process of this invention include compounds of the structures:

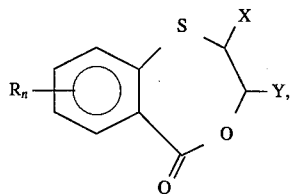

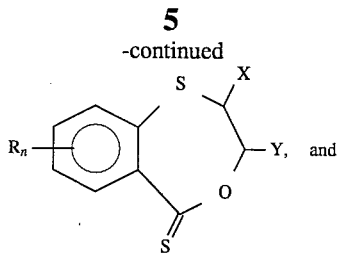

and

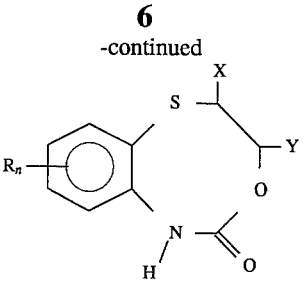

wherein X and Y together form a fused cyclopentyl or cyclohexyl ring, and n is 0 or 1. When n is 1, R is preferably $C_1$–$C_4$ alkyl, and most preferably methyl.

| Compound No. | CO-CATALYSTS OF THIS INVENTION Structure and Name | |
|---|---|---|
| 1 | 2,3-Dihydro-2,3-tetramethylene-1,5-benzo-1,4-thioxepan-5-one | (See Examples 1–6) |
| 2 | 2,3-Dihydro-2,3-tetramethylene-1,5-benzo-1,4-thioxepan-5-thione | (See Example 7) |
| 3 | 2,3-Dihydro-2,3-trimethylene-1,5-benzo-1,4-thioxepan-5-one | (See Example 8) |
| 4 | 8-Chloro-2,3-dihydro-2,3-tetramethylene-1,5-benzo-1,4-thioxepan-5-one | (See Example 9) |

-continued

CO-CATALYSTS OF THIS INVENTION

| Compound No. | Structure and Name | |
|---|---|---|
| 5 | 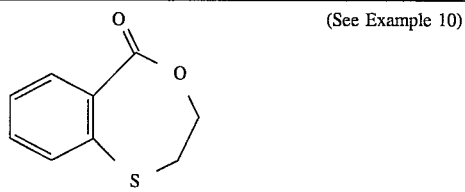<br>2,3-Dihydro-1,5-benzothioxepan-5-one | (See Example 10) |
| 6 | 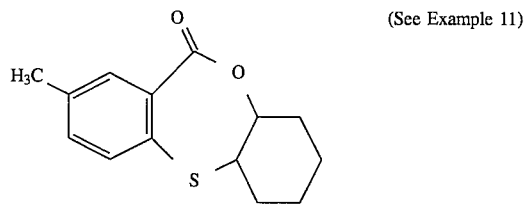<br>7-Methyl-2,3-dihydro-2,3-tetramethylene-1,5-<br>benzo-1,4-thioxepan-5-one | (See Example 11) |
| 7 | 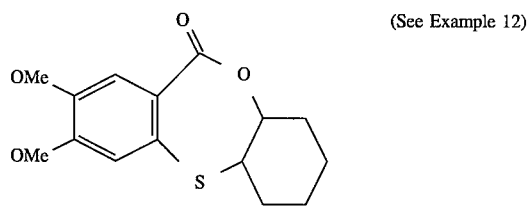<br>7,8-Dimethoxy-2,3-dihydro-2,3-tetramethylene-1,5-<br>benzo-1,4-thioxepan-5-one | (See Example 12) |
| 8 | 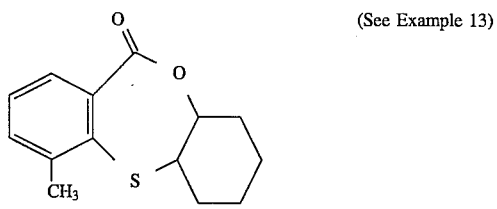<br>9-Methyl-2,3-dihydro-2,3-tetramethylene-1,5-<br>benzo-1,4-thioxepan-5-one | (See Example 13) |
| 9 | 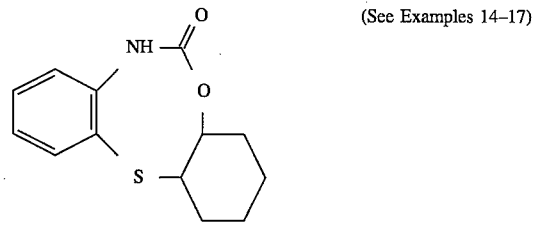<br>2,3-Dihydro-2,3-tetramethylene-1,6-benzo-<br>1,4,6-thioxazocin-5(6H)-one | (See Examples 14–17) |
| 10 | 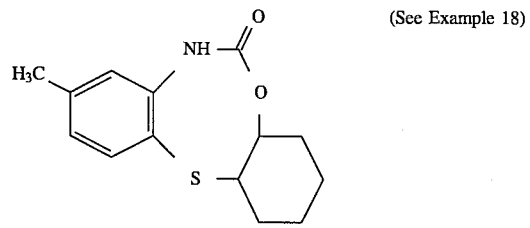 | (See Example 18) |

CO-CATALYSTS OF THIS INVENTION -continued

| Compound No. | Structure and Name | |
|---|---|---|
| 11 | 8-Methyl-2,3-dihydro-2,3-tetramethylene-1,6-benzo-1,4,6-thioxazocin-5(6H)-one 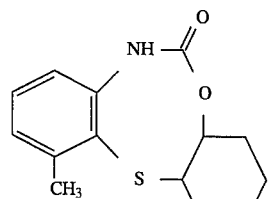 10-Methyl-2,3-dihydro-2,3-tetramethylene-1,6-benzo-1,4,6-thioxazocin-5(6H)-one | (See Example 19) |
| 12 | 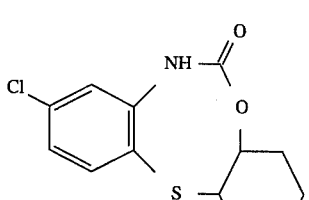 8-Chloro-2,3-dihydro-2,3-tetramethylene-1,6-benzo-1,4,6-thioxazocin-5(6H)-one | (See Example 20) |

The process of the invention is typically carried out in the liquid phase with the alkylbenzene reactant serving as solvent or primary liquid reaction medium. If desired, the reaction mixture may be diluted by addition of an inert solvent. Suitable solvents are those inert to the reactants and conditions of the process of the invention, such as methylene chloride, chloroform, and carbon tetrachloride. Preferably, the process is carried out without addition of an inert solvent.

The amounts of catalyst and co-catalyst employed may vary considerably. Substantial benefits in terms of the lowering of the ratio of ortho- to para- isomer in the product may be achieved, for example, when the co-catalyst is present in an amount sufficient to provide a molar ratio of alkylbenzene:co-catalyst ranging from less than about 500:1 to 60,000:1 or higher. The preferred alkylbenzene:co-catalyst molar ratio is between about 30,000:1 and 50,000:1.

The amounts of catalyst and co-catalyst are typically sufficient to provide a molar ratio of catalyst:co-catalyst of between about 0.01:1 and 20:1, preferably between about 0.0:1 and 10:1.

Although it is preferred to carry out the process at atmospheric pressure, sub-atmospheric or superatmospheric pressures may be employed, if desired.

Under atmospheric pressure, the chlorination of alkylbenzenes, in accordance with the present invention, may be carried out over a wide range of temperatures, ranging for example from sub-zero temperatures such as −30° C. or below to over 100° C. The upper limit of temperature is, of course, determined by the boiling point of the reaction medium, and may, depending on the boiling point limitation, range as high as 150° C. or higher. However, no practical advantage is gained through the use of higher temperatures or extremely low temperatures and it is preferred to employ temperatures in the range of about 20° to 100° C. and preferably about 40° to 60° C. The optimum temperature will vary somewhat, depending on the particular alkylbenzene and catalyst system employed.

The following specific examples are provided to further illustrate this invention and the manner in which it may be practiced.

EXAMPLES 1–6

In a glass reactor wrapped in aluminum foil, a mixture of 70.4 g (0.764 mole) of toluene, 0.0062 g (3.8×10$^{-5}$ mole) FeCl$_3$, and 0.0045 g (1.911×10$^{-5}$ mole) of 2,3-dihydro-2,3-tetramethylene-1,5-benzo-1,4-thioxepan-5-one (Formula was heated to 50° C., in a nitrogen atmosphere, and maintained thereat, with stirring, while chlorine gas was passed through the reactor at about 70 SCCM over a period of 3.25 hours. The course of the reaction was monitored using gas chromatography to follow the disappearance of toluene. When 90% of the toluene had reacted, chlorine addition was stopped and the apparatus was swept with nitrogen and cooled to room temperature. Gas chromatographic analysis of the reaction mixture indicated a 93% yield of monochlorotoluene with an o/p of 0.85.

The general procedure of Example 1 was repeated using the same reactants, catalyst and co-catalyst, varying the amounts and conditions and with the results as shown in Table 1 below.

TABLE 1

| EX | T °C. | Tol/ Cocat M.R.[a] | FeCl$_3$ Cocat M.R.[a] | o/p | Wt of Reagents (g) | | | Cl$_2$ SCCM | Time |
| --- | --- | --- | --- | --- | --- | --- | --- | --- | --- |
| | | | | | PhMe | FeCl$_3$ | Cocat | | |
| 1 | 50 | 40000 | 2.0 | 0.8500 | 70.4 | 0.0062 | 0.0045 | 70 | 3.25 |
| 2 | 50 | 2000 | 1.0 | 0.905 | 43.05 | 0.0379 | 0.0547 | 41 | 3.0 |
| 3 | 40 | 40000 | 2.0 | 0.850 | 56.8 | 0.005 | 0.0036 | 51 | 3.25 |
| 4 | 40 | 40000 | 1.0 | 0.970 | 50.0 | 0.0022 | 0.0032 | 50 | 3.5 |
| 5 | 50 | 200000 | 2.0 | 1.400[b] | 40.0 | 0.0007 | 0.0005 | 40 | 3.0 |
| 6 | 50 | 40000 | 2.0 | 0.858 | 42.0 | 0.0037 | 0.0027 | 21 | 5.75 |

[a]Mole Ratio
[b]After about 50% reaction, chlorination was inhibited.

EXAMPLES 7–13

The general procedure of Example 1 was repeated except that in place of the co-catalyst of that example, there were substituted various other co-catalysts, varying the conditions and amounts of reactants and with the results as set forth in Table II below.

TABLE II

| EX | Cocat | T °C. | Tol/ Cocat M.R.[a] | FeCl$_3$ Cocat M.R.[a] | o/p | Wt of Reagents (g) | | | Cl$_2$ SCCM | Time |
| --- | --- | --- | --- | --- | --- | --- | --- | --- | --- | --- |
| | | | | | | PhMe | FeCl$_3$ | Cocat | | |
| 7 | 2 | 50 | 40000 | 2.0 | 0.970 | 25.0 | 0.0022 | 0.0017 | 25 | 3.25 |
| 8 | 3 | 50 | 40000 | 2.0 | 0.875 | 34.1 | 0.003 | 0.002 | 34 | 3.25 |
| 9 | 4 | 50 | 40000 | 2.0 | 0.968 | 46.6 | 0.0041 | 0.0034 | 48 | 3.0 |
| 10 | 5 | 50 | 40000 | 2.0 | 1.135[b] | 45.4 | 0.004 | 0.0022 | 44 | 3.0 |
| 11 | 6 | 50 | 40000 | 2.0 | 0.827 | 48.8 | 0.0043 | 0.0033 | 48 | 3.0 |
| 12 | 7 | 50 | 40000 | 2.0 | 1.485 | 31.8 | 0.0028 | 0.0025 | 32 | 3.0 |
| 13 | 8 | 50 | 40000 | 2.0 | 0.826 | 44.3 | 0.0039 | 0.003 | 43 | 3.0 |

[a]Mole Ratio

EXAMPLES 14–17

The general procedure of Example 1 was repeated, substituting equal molar ratios of co-catalyst Compound 9 in place of co-catalyst 1. Temperature and amounts were varied with the results as shown in Examples 14–17 of Table III, below.

TABLE III

| EX | T °C. | Tol/ Cocat M.R.[a] | FeCl$_3$ Cocat M.R.[a] | o/p | Wt of Reagents (g) | | | Cl$_2$ SCCM | Time |
| --- | --- | --- | --- | --- | --- | --- | --- | --- | --- |
| | | | | | PhMe | FeCl$_3$ | Cocat | | |
| 14 | 30 | 40000 | 2.0 | 1.390[b] | 32.9 | 0.0029 | 0.0022 | 28 | 3.0 |
| 15 | 40 | 40000 | 2.0 | 0.755[c] | 64.8 | 0.0044 | 0.0044 | 65 | 2.5 |
| 16 | 50 | 40000 | 2.0 | 0.813 | 55.7 | 0.0038 | 0.0038 | 54 | 3.0 |
| 17 | 60 | 40000 | 2.0 | 0.906 | 52.3 | 0.0035 | 0.0035 | 50 | 3.0 |

[a]Mole Ratio
[b]Benzyl chloride was a minor product.
[c]o/p ratio was measured after 30% reaction.

EXAMPLES 18–20

The general procedure of the preceding examples was repeated, substituting co-catalysts 10, 11, and 12 for the co-catalysts previously employed. In each example the reaction temperature was maintained at 50° C.; the toluene: co-catalyst molar ratio was 4000; and the FeCl$_3$:co-catalyst molar ratio was 2.0. The amounts of reagents; reaction time; and o/p ratio obtained are set forth in Table IV below.

TABLE IV

| EX | Cocat | o/p | Wt of Reagents (g) PhMe | FeCl₃ | Cocat | Cl₂ SCCM | Time |
|---|---|---|---|---|---|---|---|
| 18 | 10 | 0.850 | 52.3 | 0.0046 | 0.0035 | 59 | 3.75 |
| 19 | 11 | 0.932 | 53.4 | 0.0047 | 0.0038 | 58 | 4.0 |
| 20 | 12 | 1.029 | 32.9 | 0.0029 | 0.0025 | 42 | 3.5 |

EXAMPLE 21

Preparation of 2,3-Dihydro-2,3-tetramethylene-1,5-benzo-1,4-thioexpan-5-ones (co-catalysts 1, 3, 4, 6, 7, and 8)

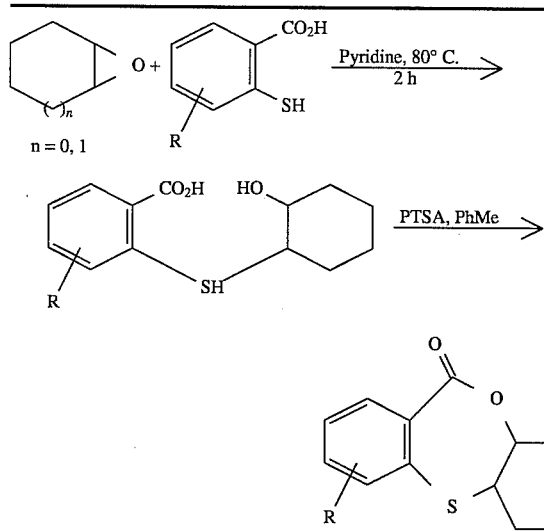

| Cocatalyst | n | R | M.P. (°C.) | Yield (%) |
|---|---|---|---|---|
| 3 | 0 | H | oil | 22 |
| 1 | 1 | H | 113.5–114.5 | 66 |
| 4 | 1 | 4-Chloro | 121–122 | 20 |
| 6 | 1 | 5-Methyl | 145–147 | 53 |
| 7 | 1 | 4,5-Dimethoxy | Gum | 12 |
| 8 | 1 | 3-Methyl | 122–123 | 13 |

GENERAL PROCEDURE

To a 0.8M solution of the appropriate 2-mercaptobenzoic acid derivative in reagent grade pyridine was added 1.1 mols of cyclopentene oxide or cyclohexene oxide and the mixture was heated at 80° C. for 2 hours. After cooling the reaction mixture to room temperature, pyridine and volatiles were removed using a water pump followed by vacuum pump (0.1 torr). The residual hydroxy acid derivative intermediate was found by GC to be sufficiently pure to take it to the next step.

The intermediate obtained above was taken in toluene so as to obtain a 0.3M solution. To this was added a catalytic amount of p-toluenesulfonic acid (PTSA) and the mixture was refluxed for 1 hour using a Dean Stark water trap. The mixture was then cooled, and water was added. The organic layer was separated, washed twice with aq. NaHCO₃ solution, dried with MgSO₄ and concentrated to give the pure lactone product.

EXAMPLE 22

Preparation of 2,3-Dihydro-2,3-tetramethylene-1,5-benzo-1,4-thioxepan-5-thione (co-catalyst (2)

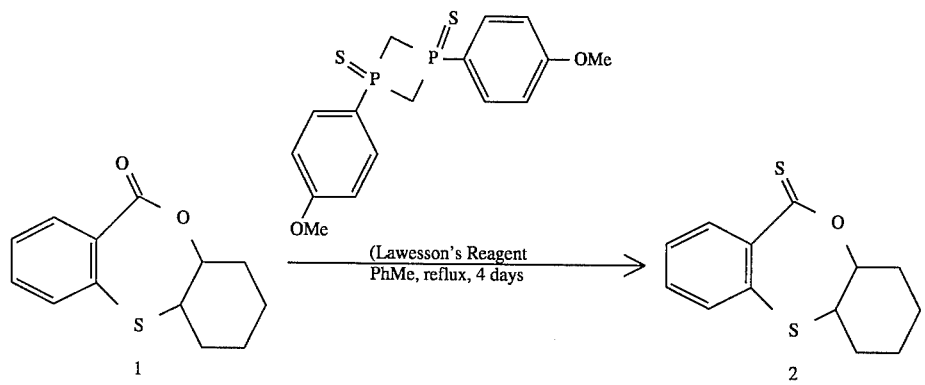

PROCEDURE

A solution of 0.181 g (0.774 mmol) of 1 in 2 mL of dry toluene was treated with 0.156 g (0.387 mmol) of Lawesson's reagent and the mixture was heated under reflux for 4 days. The reaction mixture was cooled to room temperature and the toluene was evaporated. The residue was then subjected to preparative TLC using 95/5 hexanes/ether to afford 0.16 g (83%) of pure thionolactone 2 as a light orange gum.

EXAMPLE 23

Preparation of Cyclic Urethanes (co-catalysts 9, 10, 11, and 12)

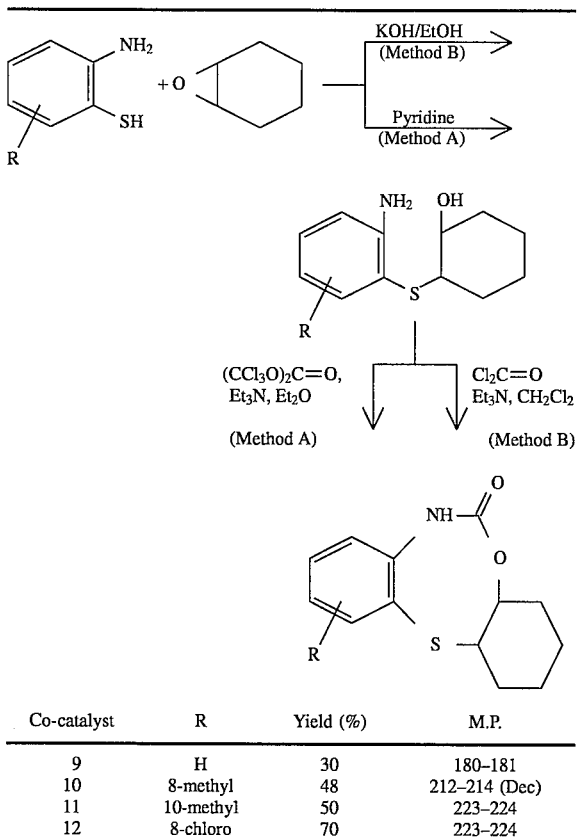

| Co-catalyst | R | Yield (%) | M.P. |
|---|---|---|---|
| 9 | H | 30 | 180–181 |
| 10 | 8-methyl | 48 | 212–214 (Dec) |
| 11 | 10-methyl | 50 | 223–224 |
| 12 | 8-chloro | 70 | 223–224 |

GENERAL PROCEDURE

Synthesis of compounds 9–12 were accomplished using either of the two pathways shown in the scheme above. A representative example of synthesis using each method is described below.

Method A. Exemplified by Synthesis of Compound 9

A mixture of 5.09 g (40.6 mmol) of 2-aminothiophenol and 4.39 g (44.7 mmol) of cyclohexene oxide in 85 mL pyridine was stirred at 80° C. for 4 hours. The reaction mixture was cooled to room temperature, and pyridine and volatiles were removed under 0.1 torr. The brown residue (7.87 g, 87% yield) solidified partly upon standing. GC analysis indicated this intermediate hydroxyacid to be sufficiently pure for further transformation.

A solution of 1.03 g (4.6 mmol) of the above hydroxyacid intermediate in a solvent mixture of 40 mL anhydrous diethyl ether and 20 mL dichloromethane was cooled to 0° C. and treated dropwise with a solution of 0.46 g (1.55 mmol) of triphosgene in 3 mL of anhydrous diethyl ether over 25 minutes. After addition, the ice bath was allowed to warm up to room temperature and stirred overnight. The reaction mixture was poured into 30 mL water and extracted with 60 mL ether. The water layer was extracted with 50 mL ether and combined ether extracts were washed with 3×100 mL saturated NaHCO$_3$ solution, then with 50 mL water, dried with MgSO$_4$ and concentrated to give the crude product. Purification by silica gel column chromatography (24 g silica gel, 20/80 hexanes/ether eluent) afforded 0.44 g (30%) of pure 9 as a pale yellow flaky solid; m.p. 180°–181° C. The material was also characterized by its proton and carbon NMR spectra.

EXAMPLE 24

Method B. Exemplified By Synthesis of Compound 10

To a solution of 2.62 g (15 mmol) of 2-amino-4-methylthiophenol hydrochloride in 5 mL of ethanol, a solution of 1.47 g (15 mmol) of cyclohexene oxide and 1.98 g (30 mmol) of KOH (85% assay) in 15 mL ethanol was added and the mixture refluxed for 1 hour under nitrogen. From the mixture, 10 mL of ethanol was then evaporated and the residue was treated with water (20 mL) to precipitate a solid which was separated by filtration. After drying at room temperature, the solid was dissolved in 50 mL of ether and solution filtered through alumina (20 g, activated, acidic, Brockmann I). The eluate was then evaporated and residue crystallized from hexane to yield 2.75 g (77%) of pure hydroxamine intermediate (2-hydroxycyclohexyl-(2-amino-4-methylphenyl)sulfide); m.p. 94°–97° C.

To a solution of 1.18 g (5 mmol) of the above intermediate hydroxyamine in 10 mL of dichloromethane, a solution of 1 mL (10 mmol) of triethylamine in 5 mL of dichloromethane was added. The mixture was cooled to –3° C. and 1.5 mL (20 mmol) of phosgene was sparged through the solution under slow nitrogen flow (<60 cc/min) for 0.5 hours. The dark blue mixture was allowed to warm to room temperature and left stirring overnight. The reaction mixture was treated with water, 5% NaHCO$_3$ aqueous solution, then water again, dried with Na$_2$SO$_4$, and filtered through alumina. Dichloromethane was evaporated from the eluate to give a solid residue which was crystallized from ethanol to afford 0.63 g (48%) of pure product (10) as colorless crystals; m.p. 212°–214° C. (dec). The material was also characterized from its proton and carbon NMR spectra.

We claim:
1. A process for the direct ring chlorination of alkylbenzenes which comprises reacting an alkylbenzene with a chlorine in the presence of a Lewis acid catalyst and a co-catalyst comprising a compound or mixture of compounds characterized by the formula:

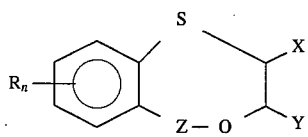

wherein Z is:

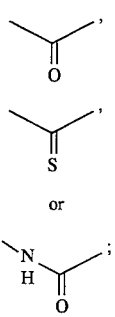

R is Cl, Br, F, $C_1$ to $C_8$ alkyl, or $C_1$ to $C_8$ alkoxy; x and y are each hydrogen, or taken together form a fused cyclopentyl or cyclohexyl ring; n is 0, 1, or 2, with the proviso that when Z is [3], n is 0 or 1.

2. A process according to claim 1 wherein the co-catalyst is a compound characterized by the formula:

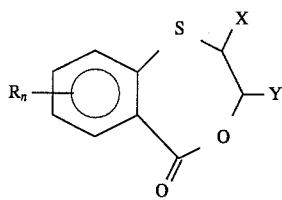

where R is $C_1$ to $C_4$ alkyl; x and y taken together, form a fused cyclopentyl or cyclohexyl ring; and n is 0 or 1.

3. A process according to claim 1 wherein the co-catalyst is a compound characterized by the formula:

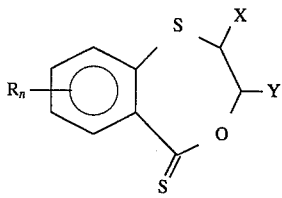

where R is $C_1$ to $C_4$ alkyl, x and y are each hydrogen, or taken together form a fused cyclopentyl or cyclohexyl ring; and n is 0 or 1.

4. A process according to claim 1 wherein the cocatalyst is a compound characterized by the formula:

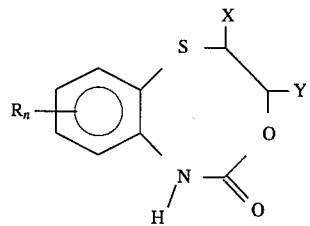

where R is $C_1$ to $C_4$ alkyl; x and y taken together, form a fused cyclopentyl or cyclohexyl ring; and n is 0 or 1.

5. A process according to claim 1 wherein the alkylbenzene is toluene.

6. A process according to claim 5 wherein the catalyst is a chloride of aluminum, antimony, or iron.

7. A process according to claim 6 wherein the catalyst is antimony trichloride.

8. A process according to claim 6 wherein the catalyst is ferric chloride.

9. A process according to claim 6 carried out at a temperature in the range of about 20° to 100° Celsius.

10. A process according to claim 9 wherein the alkylbenzene and co-catalyst are present in a molar ratio of alkylbenzene:co-catalyst of between about 30,000:1 to about 50,000:1.

11. A process according to claim 10 wherein the catalyst and co-catalyst are present in a molar ratio of between about 0.01:1 and 20:1.

12. A process according to claim 11 wherein the catalyst is $FeCl_3$.

13. A process according to claim 11 wherein R is methyl, n is 0 or 1, and x and y together form a fused cyclopentyl or cyclohexyl ring.

* * * * *